United States Patent [19]

Schwartz et al.

[11] Patent Number: 4,677,067
[45] Date of Patent: Jun. 30, 1987

[54] MAGNETOTACTIC BACTERIA IN CLINICAL ASSAY, IMMUNOASSAY, AND CELL SEPARATION PROCEDURES AND THE LIKE

[75] Inventors: Brian B. Schwartz, New York, N.Y.; Nancy Blakemore, Durham, N.H.

[73] Assignee: Bio-Magnetech Corporation, Durham, N.H.

[21] Appl. No.: 623,373

[22] Filed: Jun. 22, 1984

[51] Int. Cl.$^4$ .................. B03L 1/00; C12N 11/16; C12N 13/00; G01N 33/554

[52] U.S. Cl. .................. 435/177; 210/695; 435/262; 435/820; 436/526; 436/806; 436/824; 530/413; 530/811

[58] Field of Search .................. 435/4, 7, 29, 30, 168, 435/173, 262, 267, 268, 269, 272, 820, 6, 177; 436/527, 529, 518, 519, 531, 806, 824, 177, 178, 501, 526, 806, 824; 530/413, 811

[56] References Cited

U.S. PATENT DOCUMENTS

| | | | |
|---|---|---|---|
| 3,720,760 | 3/1973 | Bennich et al. | 436/513 |
| 3,882,225 | 5/1975 | Patel et al. | 424/11 |
| 4,385,119 | 5/1983 | Blakemore | 435/168 |

OTHER PUBLICATIONS

Baum et al. in Weetall (Ed.) "Immobilized Enzymes, Antigens, Antibodies and Peptides", Marcel Dekker, New York, 1975, pp. 431–437.
Ithakissios et al., *Clinical Chemistry* 23, 2072–2079, 1977.
Mattiasson et al., in Maggio (Ed.) "Enzyme-Immunoassay", CRC Press, Boca Raton, FL, 1980, pp. 213–248.

*Primary Examiner*—Sidney Marantz
*Assistant Examiner*—David A. Saunders
*Attorney, Agent, or Firm*—Cooper, Dunham, Griffin & Moran

[57] ABSTRACT

A method for detecting or removing a substance in a medium is presented. Magnetic material, particularly magnetic bacteria or magnetic particles contained therein, are treated to render them receptive to binding or attachment to the substance sought to be detected or removed. Following binding or attachment to the treated magnetic material, the medium is subjected to a magnetic field, which results in removal of the magnetic material and the substance bound or attached thereto.

5 Claims, No Drawings

MAGNETOTACTIC BACTERIA IN CLINICAL ASSAY, IMMUNOASSAY, AND CELL SEPARATION PROCEDURES AND THE LIKE

BACKGROUND OF THE INVENTION

The use of magnetic fields to separate magnetic material from non-magnetic material in, e.g., fluid-like media or suspensions has been recognized as a technique potentially useful in biological and biochemical separation processes. U.S. Pat. Nos. 3,700,555, and 3,970,518, e.g., disclose magnetic separation models for separating lymphocytes from blood samples, and in clinical immunoassays. The disclosures show that magnetic material may be treated so that substances, such as antigens, will attach or bind to the surface of magnetic material. Once attached or bound, these substances may be separated out of a medium when a magnetic field is applied thereto, because the magnetic field will, naturally, draw the magnetic material out of the medium. The attached substance will separate out of the medium together with the magnetic material, and may then be separated therefrom by treatment with separating agents.

One problem with the presently available methods of magnetic separation is that the particle forms of magnetic material which have been in use must be coated, or treated extensively to provide a binding or attaching site for molecular attachment. Magnetic material, unless treated, does not provide sufficient, stable attachment or binding sites for biological or biochemical material. As a result, magnetic separation techniques have been hampered either by the need for extensive pretreatment of the magnetic material, or have yielded poor results when there has been no pretreatment.

Recently, magnetotactic bacteria have been discovered in nature, and have been found to be amenable to cultivation in the laboratory. See, e.g., Frankel, Blakemore & Wolfe, *Science*, v. 203, pp. 1355–56 (1979); Maugh, *Science*, v. 215, pp. 1492–1493; Blakemore, Maratea & Wolfe, *Journal of Bacteriology*, v. 140, No. 2, pp. 720–29 (November 1979); Blakemore, *Science*, v. 190, pp. 377–79 (1975). In addition, the following U.S. patents, the disclosures of which are incorporated by reference herein, disclose aspects of magnetic or magnetotactic bacteria and their cultivation. U.S. Pat. No. 4,385,119, discloses pure cultures of a strain of magnetotactic Aquaspirillum, designated as strain MS-1 and American Type Culture Collection identification number ATCC 31632, and U.S. Pat. No. 4,394,451, discloses methods and media for culturing a magnetotactic bacteria, including strain MS-1. These magnetotactic bacteria are magnetotactic because of the presence of particles of magnetite, $Fe_3O_4$, enclosed within sheaths or membranes in the bacteria. These sheath-enclosed particles of magnetite, or magnetosomes as they are called, exist as independent particles, or in arrays or chains. The magnetosomes are, naturally, magnetic even when removed from the bacteria. The bacteria and magnetosomes possess qualities which are highly useful for use in magnetic separation methods. For example, the bacteria and magnetosomes are highly uniform in size, shape, and magnetic properties, so behavior of a sample of either magnetotactic bacteria or magnetosomes in a magnetic field gradient will be uniform, with little allowance necessary for variations in physical properties. The bacteria and magnetosomes possess high dipole moments, so these will migrate easily to a stronger magnetic field gradient. Additionally intracellular or intramembranous magnetite increases the density of the bacteria or magnetosomes, which, in terms makes both of these suitable for use in separation by centrifugation.

Hence it is an object of this invention to provide a magnetic separation method in which magnetic bacteria are used.

It is a further object of the invention to provide a method of magnetic separation wherein magnetosomes or the magnetic material therein are used.

It is a still further object of the invention to provide a method of quantitative analysis, using magnetic bacteria or magnetosomes.

How these and other objects of the invention are accomplished will become apparent in light of the accompanying disclosure.

SUMMARY OF THE INVENTION

Magnetic material derived from biological sources, such as magnetic bacteria or magnetosomes, are treated to render their sheaths or membranes susceptible to attachment by various substances. After treatment, the magnetic bacteria or magnetosomes are contacted with the medium in which the substance which is to be separated is present. This contact takes place under conditions favoring attachment and, when attachment has taken place, the medium containing the magnetic material to which the substance has been attached is subjected to a magnetic field gradient. The magnetic field gradient attracts the magnetic material, and hence the material attached thereto, to the magnetic poles. Once the magnetic material has been attracted to and held by the magnetic field gradient the medium may be removed, leaving behind only the magnetic material with the substance attached thereto. If it is desired, the magnetic material may then be removed and separated and the substance removed from attachment to the magnetic material by any suitable method for removing the substance from the substrate to which it is attached.

DETAILED DESCRIPTION OF THE INVENTION

Biological magnetic material may be derived from lysed magnetic bacteria, such as *Aquaspirillum magnetotacticum* or the whole magnetic bacteria may be used. Lysed magnetic bacteria yield magnetosomes, which consist of particles of magnetite (i.e., $Fe_3O_4$) which are surrounded by a sheath or membrane, either as individual particles or in chains of particles. Whole magnetic bacteria may also be used, as the magnetic properties of these bacteria result from the magnetic particles or magnetosomal units which are a part of the bacteria.

Both the magnetosomes and the whole bacteria possess biological membranes capable of interaction with and attachment of foreign molecules, such as antigens, antibodies, and chemically reactive groups. In order to enhance the ability of these membranes to form stable attachments to foreign molecules, the magnetosomes and whole bacteria may be treated with bifunctional cross linking reagents. Typical examples of these bifunctional cross linking reagents include cyanogen bromide, with the structure

or glutaraldehyde, which has the structure

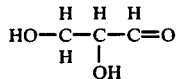

Both cyanogen bromide and glutaraldehyde act as "tanning" agents in that they render the membrane better able to form attachments, by stiffening or firming the membrane. The loss in fluidity or flexibility of the membrane makes it more likely that any bonds or attachments formed will remain stable.

When the substance sought to be removed from the medium is known to form strong attachments or bonds with a particular agent, this agent may be bonded to the membrane as well. One example of a situation where this is the case is an assay for a particular antigen. The antibody specific to the antigen is attached to treated magnetic bacteria or magnetosomes, and is then contacted with the medium containing the antigen. This method allows selective removal of the antigen from the medium containing the same when the antibody-attached magnetic bacteria or magnetosome is brought into contact therewith. One skilled in the art will recognize that not only may antigens be removed in the manner described herein, and materials such as individual protein molecules, polysaccharides, nucleic acids, lipoproteins, lipopolysaccharides, and even whole cells may be bound or attached to a receptive magnetic bacteria or magnetosome.

After the magnetosomes or magnetic bacteria have been treated, they are then introduced to the medium which contains the substance to be separated. The medium may be, e.g., a blood or serum sample, a solution of several different substances, a suspension, and the like. The magnetosomes or magnetic bacteria are introduced under conditions favoring the formation of attachments or bonds, and these conditions will differ, depending upon the nature of the materials involved. After bonding or attachment to the treated magnetic material has taken place, the medium containing the magnetic material is subjected to a magnetic field gradient which will attract and fix the magnetic material and hence the substance attached thereto. The medium which had formerly included the magnetic material is then removed, leaving behind only the magnetic material with the attached substance. The attached substance may then be removed from the magnetic material or assayed directly thereon. If it is desired, the material which has not been removed after magnetic treatment may be removed and analyzed or assayed at this time as well.

The particle of this invention allows one not only to determine when a particular substance is present, but how much of the substance is present as well. When, for example, a small sample of magnetic material with an antibody attached thereto binds antigens, the medium in which the antigen is found may then be subjected to quantitative analysis, using magnetosomes or magnetic bacteria. Further descriptive of the practice of this invention, magnetic material is treated with a cross linking reagent, and then has attached thereto an antibody. The thus treated magnetic bacteria are introduced to the sample containing the unknown amount of antigen in a measured amount exceeding the possible amount of antigen. One binding and attachment has taken place, a magnetic field is applied, and all magnetic material, including that amount which has antigen bound thereto and that which does not is separated from the medium. The same magnetic material is then introduced to a medium containing a labelled excess of antigen molecules. The labelling effect may result, e.g., from radioactivity, or enzymatic means, or any type of chemiluminescence, fluorescence, or optical means. The excess of labelled antigen will bond to any free attachment site on the magnetic particles, and following application of a magnetic field to again separate the magnetic material, the labelled antigen attached to magnetic material may be readily measured. The amount of magnetic material which is bound to labelled antigen may then be determined. Since the amount of magnetic material bound to the labelled antigen is a fraction of the total amount of magnetic material bound by antigen (labelled+unlabelled) and as the total amount of magnetic material is known, the amount of magnetic material which has unlabelled antigen attached thereto is determinable by simple subtraction. As soon as this quantity can be determined by comparison to the amounts of magnetic material bearing unlabeled standard amounts of antigen attached thereto the amount of unlabelled antigen, which is the quantity to be determined, is known.

The method described above is not limited to antigen-antibody analysis, but is applicable to any and all molecules or materials which are capable of being bound or attached to other molecules or materials. Some, but not all of such molecules or materials include proteins such as regulatory proteins and peptides, hormones, enzymes molecules, DNA and RNA fragments, catalysts, whole cells and the like, and antibiotics and other drugs.

One skilled in the art will recognize that the invention described herein is not limited to assay methods or to the specific examples discussed herein. Additional substances, such as proteins, whole cells, drugs such as antibiotics, pollutants and impurities such as metallic ions and the like may be removed, either by magnetic separation or centrifugation using biologically derived magnetic material. Additionally the medium upon which the invention may be practiced is not limited by the examples, but may extend, e.g., to solutions, suspensions, colloidal dispersions and the like as well.

What is claimed is:

1. A method for removing a substance from a medium comprising treating magnetic bacteria or magnetosomes of magnetic bacteria so as to render said magnetic bacteria or magnetosomes receptive to binding or attachment to said substance, contacting the treated magnetic bacteria or magnetosomes with the medium containing said substance to be removed to bind or attach said substance to the resulting treated magnetic bacteria or magnetosomes and subjecting the treated magnetic bacteria or magnetosomes to a magnetic field gradient so as remove said magnetic bacteria or magnetosomes, now containing said substance attached thereto, from said medium.

2. A method as in claim 1 wherein said magnetic bacteria is *Aquaspirillum magnetotacticum*.

3. A method in accordance with claim 1 wherein said substance is an antibody.

4. A method in accordance with claim 1 wherein said substance is an antigen.

5. Magnetic bacteria or magnetosomes to which has been intentionally fixed or attached thereto a substance foreign or extraneous to said magnetic bacteria or magnetosomes, wherein said substance is a member selected from the group consisting of proteins, peptides, hormones, enzymes, catalysts, DNA fragments, RNA fragments, whole cells, antibiotics, drugs, antigens and antibodies.

* * * * *